United States Patent
Hsu et al.

(10) Patent No.: US 11,827,598 B1
(45) Date of Patent: Nov. 28, 2023

(54) PREPARATION METHOD OF TOFACITINIB CITRATE

(71) Applicant: Chunghwa Chemical Synthesis & Biotech Co. Ltd., New Taipei (TW)

(72) Inventors: Yao-Lung Hsu, New Taipei (TW); Kuang-Chan Hsieh, New Taipei (TW); Hui-Wen Cheng, New Taipei (TW); Zong-Han Yang, New Taipei (TW)

(73) Assignee: CHUNGHWA CHEMICAL SYNTHESIS & BIOTECH CO. LTD., New Taipei (TW)

( * ) Notice: Subject to any disclaimer, the term of this patent is extended or adjusted under 35 U.S.C. 154(b) by 0 days.

(21) Appl. No.: 17/940,984

(22) Filed: Sep. 8, 2022

(30) Foreign Application Priority Data

Jul. 15, 2022 (TW) .................................. 111126611

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01)

(58) Field of Classification Search
CPC .......................... C07D 471/14; C07D 487/04
USPC ....................................................... 544/280
See application file for complete search history.

(56) References Cited

FOREIGN PATENT DOCUMENTS

| CN | 110343113 B | 11/2020 |
|---|---|---|
| CN | 113248509 A | 8/2021 |

OTHER PUBLICATIONS

Shuang Zhi, Dengke Liu, Ying Liu, Bingni Liu, Donghua Wang, Ligong Chen, An Efficient Method for Synthesis of Tofacitinib Citrate, J of Heterocyclic Chemistry, vol. 53, Issue 4, pp. 1259-1263 (Year: 2016).*
Price, K.E., Larrivee-Aboussafy, C., Lillie, B.M., McLaughlin, R.W., Mustakis, J., Hettenbach, K.W., Hawkins, J.M. and Vaidyanathan, R.. Mild and efficient DBU-catalyzed amidation of cyanoacetates. Organic letters, 11(9), pp. 2003-2006. (Year: 2009).*

* cited by examiner

*Primary Examiner* — Tracy Vivlemore
*Assistant Examiner* — Heather Raquel Dahlin
(74) *Attorney, Agent, or Firm* — Muncy, Geissler, Olds & Lowe

(57) ABSTRACT

The present disclosure provides a preparation method of tofacitinib citrate, which comprises the following steps: passing an intermediate TOF-2 into hydrogen at a normal pressure in the presence of a catalyst to obtain an intermediate TOF-3; in the presence of a solvent and a base, under a reduced pressure of −490 mmHg to −760 mmHg, and at a temperature of 10° C. to 25° C., reacting TOF-3 with ethyl cyanoacetate to generate an intermediate TOF-4; heating and dissolving TOF-4 and citric acid in a solvent, and performing separation by cooling to obtain tofacitinib citrate. The present disclosure obtains tofacitinib citrate with high yield, high purity and low impurities by changing a gas flow rate and a reaction temperature and pressure of a hydrogenation reaction. Therefore, the preparation method is suitable for industrial production.

10 Claims, No Drawings

PREPARATION METHOD OF TOFACITINIB CITRATE

FIELD OF TECHNOLOGY

The present disclosure belongs to the technical field of drug synthesis and particularly discloses a preparation method of tofacitinib citrate.

BACKGROUND

Rheumatoid arthritis is a systemic autoimmune disease characterized by pain and swelling of joints, and a chronic and persistent synovial inflammation of the joints, occurs at an incidence of about 0.5% in the population, and has the number of female patients 3 to 4 times that of male patients.

Tofacitinib citrate is a JAK inhibitor developed by Pfizer, USA, belongs to an inhibitor of cell information, and is mainly used for preparing a drug for treating rheumatoid arthritis. The tofacitinib citrate can directly act by entering an inner layer of inflammatory cells, and can reduce phosphorylation of STAT1 and STAT3, block message transmission of JAK1 and JAK2, and regulate expressions of interferon and interleukin so as to inhibit activation reaction of cell inflammation and reduce generation of cytokine in a physiological pathway of inflammation.

The tofacitinib citrate is generally prepared by a series of conversions of its intermediate, and the tofacitinib citrate intermediate is prepared by performing catalytic hydrogenation reaction and enabling a compound to be subjected to debenzolization reaction in the presence of hydrogen and a catalyst palladium. However, the preparation process is generally performed using a pressurizable kettle-type reactor, a reaction volume is low, a unit price is very high, a prepared single batch is low in quantity, operation time is increased, a potential manufacturing risk exists, a manufacturing cost is expensive, and therefore, the preparation process is not suitable for large-scale industrial production.

For example, as disclosed in the China invention patent of the publication No. CN113248509A, a microchannel reactor is used to perform a catalytic debenzolization reaction, but a flow rate of hydrogen in the case is defined to be 1.16-1.3 eq, which is difficult to be applied to industrial production equipment. In addition, in the China invention patent No. CN110343113B, in order to avoid a risk of an accident derived from hydrogen pressurization, sodium formate and Pd/C are used for catalysis without hydrogen, but the solid-liquid-gas three-phase reaction efficiency is a great variable. In addition, the sodium formate is easily moisturized and easily decomposed into sodium oxalate and hydrogen at a high temperature, and therefore, the sodium formate is difficult to transport.

SUMMARY

In view of the problems of a preparation process of a tofacitinib citrate intermediate industrially in the prior art, the present inventors found that the prior art does not discuss and study how to control impurities generated during the preparation process, and therefore, the present disclosure aims to provide a preparation method of tofacitinib citrate, which can obtain tofacitinib citrate with high yield, high purity, and low impurities, and is suitable for industrial production.

Therefore, the present invention is to provide a preparation method of tofacitinib citrate, comprising: step (1) passing an intermediate TOF-2 of the following formula into hydrogen at a normal pressure in the presence of a catalyst to obtain an intermediate TOF-3 of the following formula; step (2) in the presence of a solvent and a base, under a reduced pressure of −490 mmHg to −760 mmHg, and at a temperature of 10° C. to 25° C., reacting TOF-3 with ethyl cyanoacetate to generate an intermediate TOF-4 of the following formula; and step (3) heating and dissolving TOF-4 and citric acid in a solvent, and performing separation by cooling to obtain tofacitinib citrate

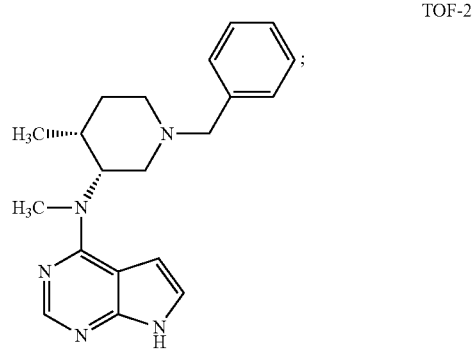

TOF-2

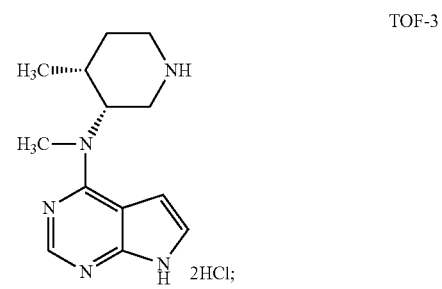

TOF-3

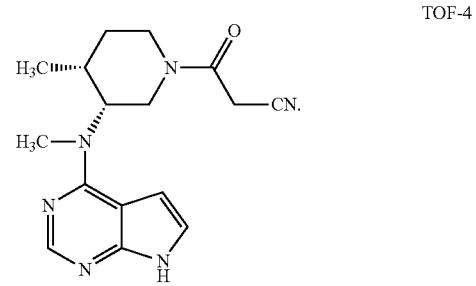

TOF-4

According to one or more embodiments of the present invention, TOF-2 is obtained by reacting BDPA of the following formula with CTP of the following formula in the presence of a solvent and a base

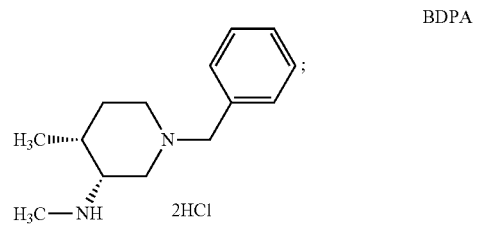

BDPA

CTP

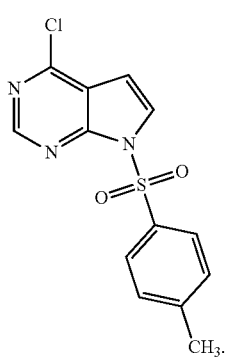

According to one or more embodiments of the present invention, the solvent is dimethyl sulfoxide (DMSO), 1-butanol (n-butanol) or water.

According to one or more embodiments of the present invention, the base is N,N-diisopropylethylamine, 2,4,6-trimethyl-pyridine, 2,3,5-collidine, potassium carbonate, cesium carbonate or tert-butanol.

According to one or more embodiments of the present invention, in step (1), a weight ratio of a flow rate of hydrogen per minute and the intermediate TOF-2 is 0.3-1.05 mL/g.

According to one or more embodiments of the present invention, the catalyst in step (1) is Pd/C, Pd(OH)$_2$/C or Pd(PPh$_3$)$_4$/C.

According to one or more embodiments of the present invention, in step (1), a weight ratio of the catalyst and the intermediate TOF-2 is 0.0032 to 0.0159.

According to one or more embodiments of the present invention, the solvent used in step (2) is toluene, ethanol, methanol, dimethylformamide, and N-methyl-2-pyrrolidone or dimethyl sulfoxide.

According to one or more embodiments of the present invention, the base used in step (2) is 1,8-diazabicyclo[5.4.0]undec-7-ene (DBU).

According to one or more embodiments of the present invention, no activated carbon is added in step (3), and a generated impurity (of the following formula TOF-IP A) is less than 0.2%

TOF IP A

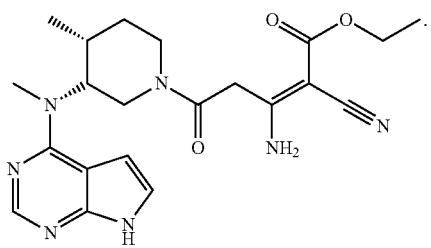

Compared with the prior art, the preparation method of tofacitinib citrate of the present disclosure has the following advantages.

(1) According to the preparation method of tofacitinib citrate of the present disclosure, no specially manufactured hydrogenation equipment is needed and a general industrial production reaction tank is used flexibly by a factory as scheduled, and therefore a manufacturing cost of special equipment is greatly reduced.

(2) In the method of the present disclosure, a hydrogen flow rate used in hydrogenation reaction is not large, no splashing occurs in the reaction tank, micro-bubbling presents on a liquid surface, a risk of over-exposure of hydrogen can be reduced, and therefore the method is low-risk.

(3) A good design is developed aiming at the preparation process, the content of the impurity TOF IP A of the prepared tofacitinib citrate by the method of the present disclosure meets the standards of International Council for Harmonisation (ICH), and therefore, medication safety is improved.

All publications and patent applications cited in this specification are incorporated herein by reference, each of which is incorporated by reference, expressly in their respective entireties, for any purposes. In case of conflict between the specification and any publications or patent applications incorporated herein, the present specification will control.

As used herein, the terms "including", "having" and "comprising" shall be construed as open-ended and non-restrictive. The singular forms "a" "an" and "the" include plural references. The term "one or more" means "at least one" and may include a single feature or mixed/combined features.

This part of the specification aims to provide a brief summary of the invention so as to enable a basic understanding of the invention. The brief summary of the invention is neither a complete description of the invention nor intended to point out the important or key elements of certain embodiments of the invention or define the scope of the invention.

DESCRIPTION OF THE EMBODIMENTS

In order to make the description of the present disclosure more detailed and complete, the following provides an illustrative description for the embodiments and specific examples of the present disclosure, but this is not the only form of implementing or using the specific examples of the present disclosure. In the description and the scope of the appended claims, unless otherwise stated in the context, "a" and "the" may also be construed as plural.

The present disclosure provides a preparation method of tofacitinib citrate. A synthetic route is as the following processes comprising three steps of step (1), step (2), and step (3).

Step (1)

In the presence of a catalyst, an intermediate (3R,4R)-(1-benzyl-4-methylpiperidin-3-yl)methyl-(7H-pyrrolo[2,3-d]pyrimidine-4-yl)amine (TOF-2) is passed into hydrogen at a set hydrogen flow rate at a normal pressure to obtain an intermediate (3R,4R)-(4-methylpiperidin-3-yl)-methyl-(7H-pyrrolo[2,3-d]pyrimidin-4-yl) (TOF-3), wherein, in an embodiment of the present disclosure, TOF-2 is dissolved in acetic acid and ethanol for reaction at a dissolving temperature of 40° C. to 60° C., such as 40° C., 45° C., 50° C., 55° C. or 60° C.; and after the dissolving reaction is completed, nitrogen is introduced into a liquid surface for one minute, and hydrogen is introduced. In the present disclosure, the flow rate of the hydrogen is set as a ratio of the flow rate of the hydrogen introduced per minute and the weight of the intermediate TOF-2 of 0.3-1.05 mL/g, such as 0.3 mL/g, 0.35 mL/g, 0.55 mL/g, 0.75 mL/g, 0.85 mL/g, 0.95 mL/g or 1.05 mL/g, preferably 0.3 mL/g, 0.33 mL/g, 1 mL/g or 1.048 mL/g. In addition, in another embodiment of the present disclosure, after the reaction is completed, the nitrogen is further introduced into the liquid surface for one minute and suction filtration is assisted using diatomite; and a strong acid (for example, hydrochloric acid) is added to form a salt and precipitate to obtain TOF-3. In one embodiment of the present disclosure, a temperature of adding the strong acid to form a salt is controlled at 8±5° C. and stirring is performed (about 60 min). In another preferred embodiment, TOF-3 is further dried through a vacuum oven at a temperature set to 60° C. to 80° C., such as 60° C., 65° C., 70° C., 75° C. or 80° C. and a pressure set below −700 mmHg.

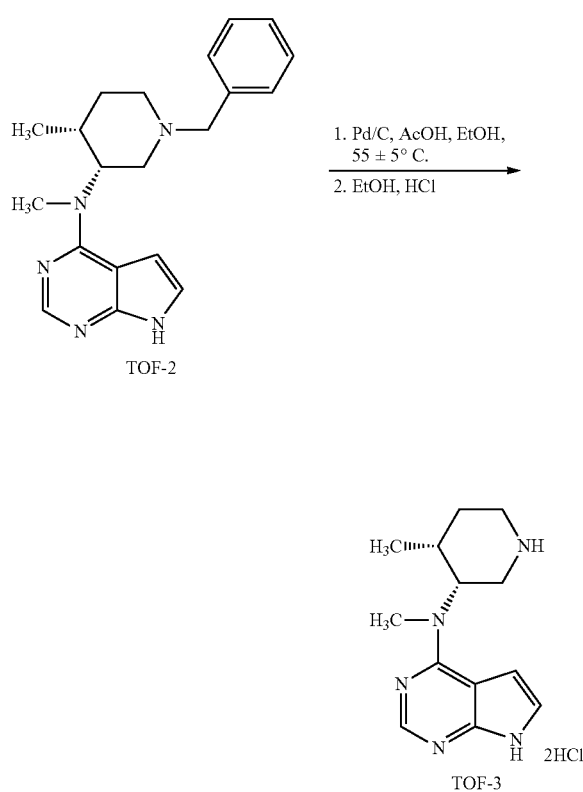

TOF-2

1. Pd/C, AcOH, EtOH, 55 ± 5° C.
2. EtOH, HCl

TOF-3

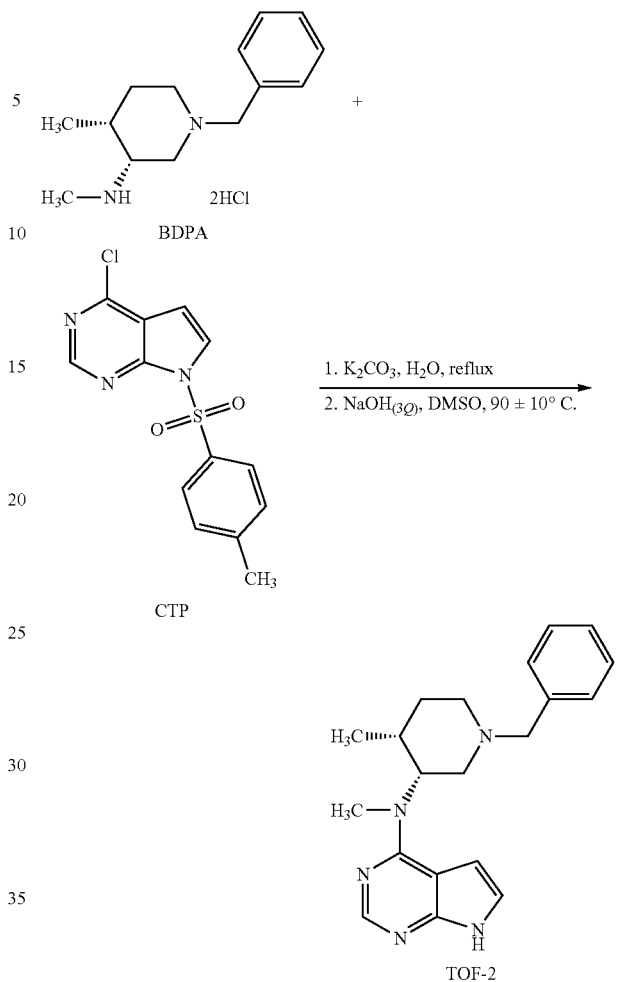

BDPA

CTP

1. K₂CO₃, H₂O, reflux
2. NaOH(aq), DMSO, 90 ± 10° C.

TOF-2

In a preferred embodiment, the catalyst in step one is: Pd(OH)2/C, Pt/C, Pd/C, Pd(OH)2/Al2O3, Pd/Al2O3 or Pd(PPh3)4/C. Since palladium has a high activity and is bound to activated carbon, thereby reducing risks of use and transportation, a catalyst of palladium can be preferably used for catalysis. Therefore, in a preferred embodiment of the present disclosure, the catalyst is Pd/C, Pd(OH)2/C or Pd(PPh3)4/C.

In a preferred embodiment, a weight ratio of the catalyst in step one and the intermediate TOF-2 is 0.0032 to 0.0159, preferably, 0.0032 to 0.0048, such as but not limited to 0.0035, 0.0038, 0.0040, 0.0042, 0.0046, and 0.0048.

In the present disclosure, there is no limitation on how to prepare TOF-2 which can be obtained by a commonly known preparation method. In a preferred embodiment, in the present of a solvent and a base, (3R,4R)-1-benzyl-N-4-dimethylpiperidine-3-amine dihydrochloride (BDPA) is added into 4-chloro-7-tosyl-7H-pyrolo(2,3-D)pyrimidine (CTP) to perform an aromatic nucleophilic substitution reaction (SNAr reaction) to remove protection of p-toluene-sulfonyl (tosyl) to prepare the intermediate TOF-2.

In the process of preparing the intermediate TOF-2, a step of adding a strong base to remove a p-toluenesulfonyl protecting group is mostly heterogeneous reaction using the technology of the existing literature, and thus there is a risk of incomplete reaction. Besides, it is known that the p-toluenesulfonyl is a genotoxic impurity, which is a major concern in industrial production. In the present disclosure, the step is converted into a homogeneous reaction, such that the reaction is thorough and the genotoxic impurity p-toluenesulfonate and the catalyst toxicant can be effectively removed.

In a preferred embodiment, the solvent is dimethyl sulfoxide (DMSO), 1-butanol (n-butanol), water or a combination of the above solvents in the step of preparing the intermediate TOF-2.

In a preferred embodiment, the base added in the prepared intermediate TOF-2 may be N,N-diisopropylethylamine, 2,4,6-trimethyl-pyridine, 2,3,5-collidine, potassium carbonate, cesium carbonate or tert-butanol.

Step (2)

In the presence of a solvent and a base, the intermediate TOF-3 reacts with ethyl cyanoacetate to generate the intermediate 3-[(3R,4R)-4-methyl-3-[methyl(7H-pyrrolo[2,3-d] pyrimidin-4-yl)amino]piperidin-1-yl]-3-oxopropanenitrile (TOF-4). In one embodiment of the present disclosure, a reaction temperature of step (2) is controlled in a range below 25° C., such as between 10° C. and 25° C., for example, 10° C., 11° C., 12° C., 13° C., 14° C., 15° C., 16° C., 17° C., 18° C., 19° C., 20° C., 21° C., 22° C., 23° C., 24° C. or 25° C. (wherein the term "between" includes upper and lower endpoints); after a reactant is completely dissolved in a solvent, a vacuum pump is turned on, and a vacuum pressure is controlled in a reduced pressure environment of −490 mmHg to −760 mmHg, and the pressure may be but not limited to −490 mmHg, −500 mmHg, −550 mmHg, −600 mmHg, −650 mmHg, −700 mmHg or −750 mmHg. In one embodiment of the present disclosure, after the reaction is completed, generated TOF-4 can be collected in the following manner: removing vacuum, adding dichloromethane and hydrochloric acid at a normal pressure for extraction, and collecting a hydrochloric acid aqueous solution; adding dichloromethane into the hydrochloric acid aqueous layer, adjusting a pH value to be greater than 10.5 under mixing and stirring, and collecting a dichloromethane solution; and concentrating the dichloromethane solution to obtain a TOF-4 solid.

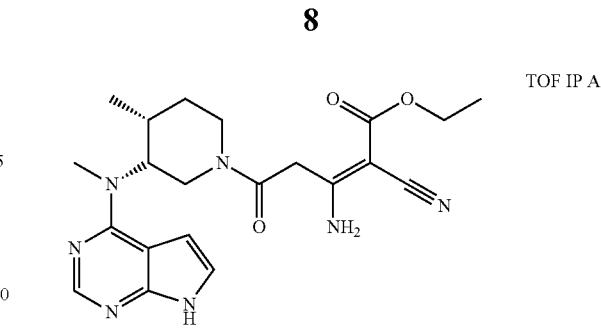

Step (3)

The intermediate TOF-4 and citric acid are heated in a solvent (the solvent may be water, methanol, butanone or a combination thereof) to be fully dissolved, a solid is separated out by cooling, filtration and drying are performed to obtain high-purity tofacitinib citrate.

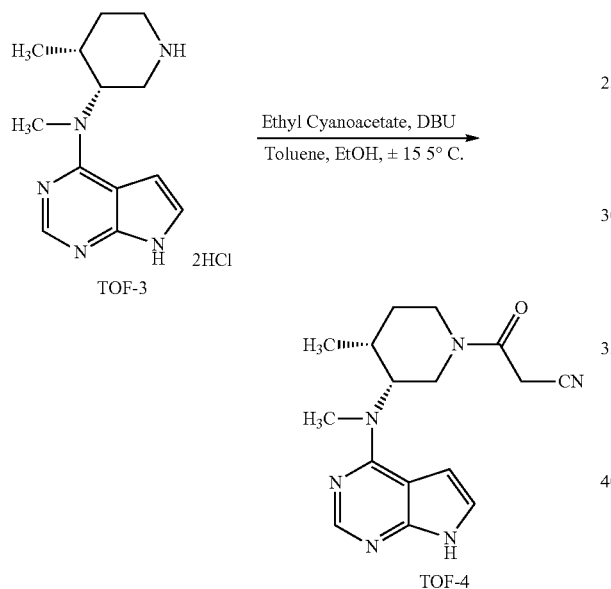

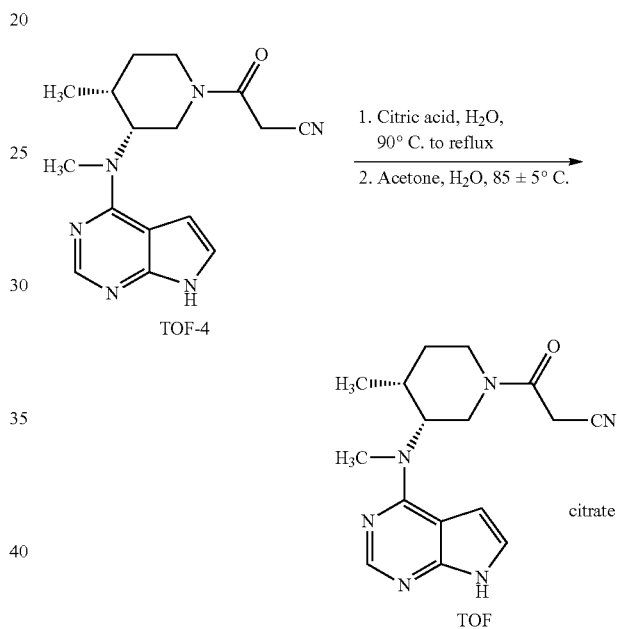

In a preferred embodiment, the solvent used in step two is toluene, ethanol, methanol, dimethylformamide, and N-methyl-2-pyrrolidone or dimethyl sulfoxide.

In a preferred embodiment, the base used in step two may be 1,8-diazabicyclo[5.4.0]undec-7-ene (DBU), N,N-diisopropylethylamin (i-Pr2NEt), N-ethylmorpholine, N,N,N',N'-tetramethylethylenediamine (TMEDA), 1-butylimidazole or N-(4-pyridyl)dimethylamine (DMAP), and preferably, the base is 1,8-diazabicyclo[5.4.0]undec-7-ene (DBU).

In the present disclosure, the inventor found that if the reaction temperature in step (2) is higher, an impurity (E)-ethyl 3-amino-2-cyano-5-43R,4R)-4-methyl-3-(methyl (7H-pyrrolo[2,3-d]pyrimidin-4-yl)amino)piperidin-1-yl)-5-oxopent-2-enoate (TOF IP A) of the following formula is more easily generated. If too many impurities are generated, a subsequent crystallization process requires multiple processes to reduce a proportion of the impurity TOF IP A. A reduced-pressure and low-temperature process in step (2) of the present disclosure can control the impurity TOF IP A generated in step (2) to be less than 0.2%, preferably less than 0.16%, 0.15%, 0.14% or 0.13%.

In an embodiment of the present disclosure, the temperature of the cooling is controlled within a range of 20° C. or less, such as between 0° C. and 20° C., for example 2° C., 4° C., 6° C., 8° C., 10° C., 12° C. ° C., 14° C., 16° C., 18° C., or 20° C. (the term "between" herein includes upper and lower endpoints).

In a preferred embodiment, no activated carbon is added in step (3), and a generated impurity TOF-IP A in a final product is less than 0.2%, preferably less than 0.1%, such as but not limited to 0.07%. %, 0.06%, 0.05%, 0.04%, 0.03% or 0.02%.

EXAMPLES

The following non-limiting examples of aspects of the present disclosure are provided primarily to illustrate the aspects of the present disclosure and the achieved benefits.

The following provides a non-limiting preparation method of tofacitinib citrate intermediates. Ten non-limiting examples (examples 1-10) are prepared according to the methods disclosed below. However, the specific methods for preparing examples 1-10 may differ from the methods disclosed below in one or more respects while remaining within the scope of the present disclosure.

Example 1: Preparation of Intermediate TOF-3

100.01 g of TOF-2, 43.88 g of acetic acid, and 711.07 g of ethanol are weighed into a reaction flask, an obtained mixture was heated to 55° C. and stirred until dissolved, 3.17 g of 10% Pd/C was added, nitrogen was introduced into a liquid surface under a normal pressure for one minute, and hydrogen was introduced at a hydrogen flow rate set to 30 mL/min. After 8 h, the reaction was complete, the nitrogen was introduced into the liquid surface for one minute, diatomite was used to assist in suction filtration to obtain a light yellow liquid, 83.91 g of hydrochloric acid was added, and a temperature was controlled at 30±10° C.; after the hydrochloric acid was added, the temperature was controlled at 8±5° C. and stirring was performed for 60 min; and a grey white solid was obtained via suction filtration. Drying was performed through a vacuum oven at a temperature set at 75° C. and a pressure below −700 mmHg, and finally a grey white solid was obtained at a yield of 99.61% and a purity of 99.44%.

Example 2: Preparation of Intermediate TOF-3

The intermediate TOF-3 of example 2 was prepared using a preparation process similar to that of the intermediate TOF-3 of example 1. However, when the intermediate TOF-3 of example 2 was prepared, 135.00 g of TOF-2, 59.32 g of acetic acid, and 1065.15 g of ethanol are weighed into a reaction flask, an obtained mixture was heated to 55° C. and stirred until dissolved, and 6.426 g of 10% Pd/C was added; a hydrogen flow rate was set to be 45 mL/min; 4 h after the reaction was completed, 130.95 g of hydrochloric acid was added, and a temperature was controlled at 30±10° C.; and the yield was 99.57% and the purity was 98.92%.

Example 3: Preparation of Intermediate TOF-3

The intermediate TOF-3 of example 3 was prepared using a preparation process similar to that of the intermediate TOF-3 of example 1. However, when the intermediate TOF-3 of example 3 was prepared, 6.68 kg of TOF-2, 2.93 kg of acetic acid, and 52.71 kg of ethanol are weighed into a reaction flask, an obtained mixture was heated to 55° C. and stirred until dissolved, and 0.32 kg of 10% Pd/C was added; a hydrogen flow rate was set to be 7 mL/min; 15 h after the reaction was completed, 5.611 kg of hydrochloric acid was added, and a temperature was controlled at 30±10° C.; and the yield was 99.54% and the purity was 99.85%.

Example 4: Preparation of Intermediate TOF-3

The intermediate TOF-3 of example 4 was prepared using a preparation process similar to that of the intermediate TOF-3 of example 1. However, when the intermediate TOF-3 of example 4 was prepared, 100.00 g of TOF-2, 43.93 g of acetic acid, and 789.01 g of ethanol are weighed into a reaction flask, an obtained mixture was heated to 55° C. and stirred until dissolved, and 3.174 g of 10% Pd/C was added; a hydrogen flow rate was set to be 100 mL/min; 22 h after the reaction was completed, 83.91 g of hydrochloric acid was added, and a temperature was controlled at 30±10° C.; and the yield was 99.46% and the purity was 99.78%.

Table 1 shows preparation parameters, yield, and purity of the intermediate TOF-3 in each example.

TABLE 1

| Examples | Hydrogen flow rate (mL/min) | Weight ratio of hydrogen flow rate to TOF-2 (mL/g) | Weight ratio of catalyst to TOF-2 | Yield (%) | Purity (%) |
| --- | --- | --- | --- | --- | --- |
| Example 1 | 30 | 0.30 | 0.0032 | 99.61 | 99.44 |
| Example 2 | 45 | 0.33 | 0.0048 | 99.57 | 98.92 |
| Example 3 | 7000 | 1.05 | 0.0048 | 99.54 | 99.85 |
| Example 4 | 100 | 1 | 0.0032 | 99.46 | 99.78 |

Example 5: Preparation of Intermediate TOF-4

100.18 g of TOF-3, 280.12 g of ethyl cyanoacetate, 251.01 g of DBU, 438.594 g of toluene, and 79.82 g of ethanol were weighed in a reaction flask, an obtained mixture was stirred until dissolved at a temperature controlled under 20° C.; after the mixture was completely dissolved, a vacuum pump was turned on with a vacuum pressure controlled at −500±10 mmHg; after 6 h, the reaction was completed, vacuum was removed, 1345.63 g of dichloromethane and 1011.750 g of 1N hydrochloric acid were added for extraction under a normal pressure, and a hydrochloric acid aqueous solution was collected; 1345.63 g of dichloromethane was added to the aqueous hydrochloric acid layer, 8N NaOH was used to adjust the pH value to be greater than 10.5 under stirring and mixing, and a dichloromethane solution was collected; and the dichloromethane solution was concentrated to obtain a light yellow solid with a yield of 99.75%, a purity of 98.85%, and an impurity TOF IP A of 0.15%.

Example 6: Preparation of Intermediate TOF-4

The intermediate TOF-4 of example 6 was prepared using a preparation process similar to that of the intermediate TOF-4 of example 5. 93.72 g of TOF-3, 259.48 g of ethyl cyanoacetate, 232.51 g of DBU, 468.60 g of toluene, and 73.95 g of ethanol were weighed in a reaction flask, an obtained mixture was stirred until dissolved at a temperature controlled under 13±3° C.; after the mixture was completely dissolved, a vacuum pump was turned on with a vacuum pressure controlled at −650±10 mmHg; after 10 h, the reaction was completed, vacuum was removed, 1246.48 g of dichloromethane and 937.20 g of 1N hydrochloric acid were added for extraction under a normal pressure, and a hydrochloric acid aqueous solution was collected; 1246.48 g of dichloromethane was added to the aqueous hydrochloric acid layer, 8N NaOH was used to adjust the pH value to be greater than 10.5 under stirring and mixing, and a dichloromethane solution was collected; and the dichloromethane solution was concentrated to obtain a light yellow solid with a yield of 99.15%, a purity of 99.12%, and an impurity TOF IP A of 0.15%.

Example 7: Preparation of Intermediate TOF-4

The intermediate TOF-4 of example 7 was prepared using a preparation process similar to that of the intermediate TOF-4 of example 5. 120.00 g of TOF-3, 332.30 g of ethyl cyanoacetate, 297.60 g of DBU, 520.20 g of toluene, and 94.68 g of ethanol were weighed in a reaction flask, an obtained mixture was stirred until dissolved at a temperature controlled under 22±3° C.; after the mixture was completely dissolved, a vacuum pump was turned on with a vacuum pressure controlled at −750±10 mmHg; after 10 h, the reaction was completed, vacuum was removed, 2122.68 g of dichloromethane and 1200.01 g of 1N hydrochloric acid were added for extraction under a normal pressure, and a hydrochloric acid aqueous solution was collected; 2122.68 g of dichloromethane was added to the aqueous hydrochloric acid layer, 8N NaOH was used to adjust the pH value to be greater than 10.5 under stirring and mixing, and a dichloromethane solution was collected; and the dichloromethane solution was concentrated to obtain a light yellow solid with a yield of 99.01%, a purity of 98.34%, and an impurity TOF IP A of 0.13%.

Example 8: Preparation of Intermediate TOF-4

The intermediate TOF-4 of example 8 was prepared using a preparation process similar to that of the intermediate TOF-4 of example 5. 5.86 kg of TOF-3, 16.22 kg of ethyl cyanoacetate, 14.53 kg of DBU, 25.40 g of toluene, and 4.62 g of ethanol were weighed in a reaction flask, an obtained mixture was stirred until dissolved at a temperature controlled under 15±5° C.; after the mixture was completely dissolved, a vacuum pump was turned on with a vacuum pressure controlled at −750±10 mmHg; after 4 h, the reaction was completed, vacuum was removed, 76.18 kg of dichloromethane and 58.6 kg of 1N hydrochloric acid were added for extraction under a normal pressure, and a hydrochloric acid aqueous solution was collected; 76.18 kg of dichloromethane was added to the aqueous hydrochloric acid layer, 8N NaOH was used to adjust the pH value to be greater than 10.5 under stirring and mixing, and a dichloromethane solution was collected; and the dichloromethane solution was concentrated to obtain a light yellow solid with a yield of 99.39%, a purity of 99.49%, and an impurity TOF IP A of 0.16%.

Comparative Example 1: Preparation of Intermediate TOF-4

The intermediate TOF-4 of example 1 was prepared using a preparation process similar to that of the intermediate TOF-4 of example 5. 106.83 g of TOF-3, 295.78 g of ethyl cyanoacetate, 265.04 g of DBU, 463.11 g of toluene, and 106.83 g of ethanol were weighed in a reaction flask, an obtained mixture was stirred until dissolved at a temperature controlled under 50±5° C.; after the mixture was completely dissolved, a vacuum pump was turned on with a vacuum pressure controlled at −750±10 mmHg; after 4 h, the reaction was completed, vacuum was removed, 1068.3 g of dichloromethane and 1068.3 g of 1N hydrochloric acid were added for extraction under a normal pressure, and a hydrochloric acid aqueous solution was collected; 1068.3 g of dichloromethane was added to the aqueous hydrochloric acid layer, 8N NaOH was used to adjust the pH value to be greater than 10.5 under stirring and mixing, and a dichloromethane solution was collected; and the dichloromethane solution was concentrated to obtain a light yellow solid with a yield of 96.58%, a purity of 98.48%, and an impurity TOF IP A of 0.73%.

Comparative Example 2: Preparation of Intermediate TOF-4

The intermediate TOF-4 of example 2 was prepared using a preparation process similar to that of the intermediate TOF-4 of example 5. 87.03 g of TOF-3, 240.96 g of ethyl cyanoacetate, 215.92 g of DBU, 377.28 g of toluene, and 87.03 g of ethanol were weighed in a reaction flask, an obtained mixture was stirred until dissolved at a temperature controlled under 70±5° C.; after the mixture was completely dissolved, a vacuum pump was turned on with a vacuum pressure controlled at −750±10 mmHg; after 4 h, the reaction was completed, vacuum was removed, 870.30 g of dichloromethane and 870.30 g of 1N hydrochloric acid were added for extraction under a normal pressure, and a hydrochloric acid aqueous solution was collected; 870.30 g of dichloromethane was added to the aqueous hydrochloric acid layer, 8N NaOH was used to adjust the pH value to be greater than 10.5 under stirring and mixing, and a dichloromethane solution was collected; and the dichloromethane solution was concentrated to obtain a light yellow solid with a yield of 95.93%, a purity of 97.32%, and an impurity TOF IP A of 1.51%.

Comparative Example 3: Preparation of Intermediate TOF-4

The intermediate TOF-4 of example 3 was prepared using a preparation process similar to that of the intermediate TOF-4 of example 5. 93.72 g of TOF-3, 259.48 g of ethyl cyanoacetate, 235.51 g of DBU, 468.60 g of toluene, and 93.72 g of ethanol were weighed in a reaction flask, an obtained mixture was stirred until dissolved at a temperature controlled under 90±5° C.; after the mixture was completely dissolved, a vacuum pump was turned on with a vacuum pressure controlled at −750±10 mmHg; after 4 h, the reaction was completed, vacuum was removed, 937.20 g of dichloromethane and 937.20 g of 1N hydrochloric acid were added for extraction under a normal pressure, and a hydrochloric acid aqueous solution was collected; 937.20 g of dichloromethane was added to the aqueous hydrochloric acid layer, 8N NaOH was used to adjust the pH value to be greater than 10.5 under stirring and mixing, and a dichloromethane solution was collected; and the dichloromethane solution was concentrated to obtain a light yellow solid with a yield of 94.33%, a purity of 97.01%, and an impurity TOF IP A of 2.11%.

Table 2 shows preparation parameters, yield, and purity of the intermediate TOF-4 in each example and comparative example

TABLE 2

| Examples | Temperature ±5 (° C.) | Pressure ±10 (mmHg) | Yield (%) | Purity (%) | Impurity (%) |
|---|---|---|---|---|---|
| Example 5 | 20 | −500 | 99.75 | 98.85 | 0.15 |
| Example 6 | 13 | −650 | 99.15 | 99.12 | 0.15 |
| Example 7 | 22 | −750 | 99.01 | 98.34 | 0.13 |
| Example 8 | 15 | −750 | 99.39 | 99.49 | 0.16 |
| Comparative example 1 | 50 | −750 | 96.58 | 98.48 | 0.73 |
| Comparative example 2 | 70 | −750 | 95.93 | 97.32 | 1.51 |
| Comparative example 3 | 90 | −750 | 94.33 | 97.01 | 2.11 |

Example 9: Preparation of Crude Product TOF-C 120.00 g of TOF-4, 243.60 g of citric acid anhydrous, and 3360.01 g of H2O were weighed into a reaction flask, heated to reflux and stirred; and after the materials were completely dissolved, the dissolved materials were slowly cooled down until a solid is precipitated, and a final temperature was maintained at 10±8° C. continuously for 3 h. A white solid was obtained via suction filtration. Drying was performed through a vacuum oven at a temperature set at 75° C. and a pressure below −700 mmHg, and finally a white solid was obtained at a yield of 98.17%, a purity of 99.70%, and an impurity TOF IP A of 0.07%.

Example 10: Preparation of Finished Product TOF 159.22 g of TOF-C, 2621.01 g of acetone, and 2229.03 g of H2O were weighed into a reaction flask, heated to reflux and stirred; and after the materials were completely dissolved, the dissolved materials were slowly cooled down until a solid is precipitated, and a final temperature was maintained at 10±8° C. continuously for 3 h. A white solid was obtained via suction filtration. Drying was performed through a vacuum oven at a temperature set at 75° C. and a pressure below −700 mmHg, and finally a white solid was obtained at a yield of 90.82%, a purity of 99.86%, and an impurity TOF IP A of 0.02%.

According to examples 7-8 in Table 2, when the reaction temperature was between 10° C. and 25° C., the vacuum pressure was controlled at −750±10 mmHg, the yield and the purity of the intermediate TOF-4 both can be as high as 99.85% or more, and the impurity was less than 0.2%. According to comparative examples 1-3 in Table 2, when the reaction temperature was higher than 25° C., even if the vacuum pressure was controlled at −750±10 mmHg, the yield and the purity of the intermediate TOF-4 were both lower than 99.85% and the impurity was all higher than 0.7%.

In summary, the preparation method of tofacitinib citrate of the present disclosure does not require specially manufactured hydrogenation equipment and a general industrial production reaction tank is used, and therefore a manufacturing cost of special equipment is greatly reduced. Moreover, a hydrogen flow rate used in hydrogenation reaction is not large, no splashing occurs in the reaction tank, which is a low-risk method. In addition, regulating the hydrogen flow can reduce the amount of palladium catalyst used to reduce industrial production costs; it can also be made for process development. With good design, the content of the impurity TOF IP A meets the standards of International Council for Harmonisation (ICH), and improve medication safety.

While a detailed description of the present invention has been given above, it should be understood that the foregoing embodiments are only some preferred ones of the invention and are not intended to be restrictive of the scope of the invention. Any equivalent change or modification that is based on the appended claims shall fall within the scope of the invention.

What is claimed is:
1. A preparation method of tofacitinib citrate, comprising
   (1) passing an intermediate TOF-2 of the following formula into hydrogen in the presence of a catalyst to obtain an intermediate TOF-3 of the following formula;
   (2) in the presence of a solvent and a base, under a reduced pressure of −490 mmHg to −760 mmHg, and at a temperature of 10° C. to 25° C., reacting TOF-3 with ethyl cyanoacetate to generate an intermediate TOF-4 of the following formula; and
   (3) heating and dissolving TOF-4 and citric acid in a solvent, and performing separation by cooling to obtain tofacitinib citrate;

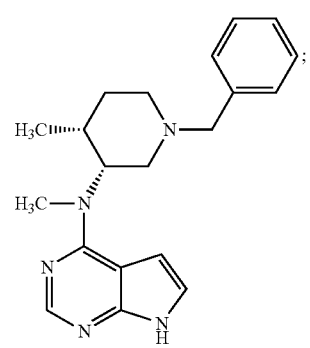
TOF-2

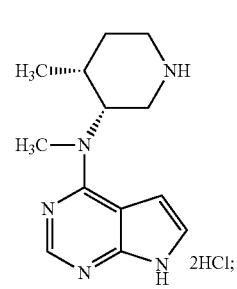
TOF-3

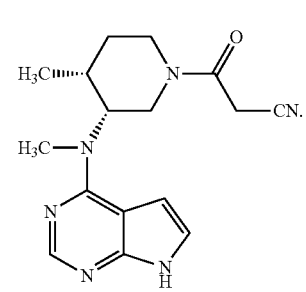
TOF-4

2. The preparation method according to claim 1, wherein TOF-2 is obtained by reacting BDPA of the following formula with CTP of the following formula in the presence of a solvent and a base

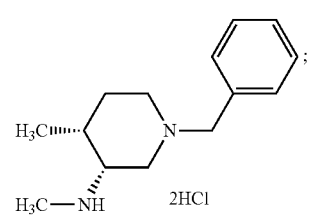
BDPA

CTP

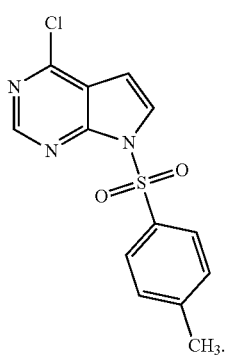

3. The preparation method according to claim 2, wherein the solvent is dimethyl sulfoxide (DMSO), 1-butanol (n-butanol) or water.

4. The preparation method according to claim 2, wherein the base is N,N-diisopropylethylamine, 2,4,6-trimethylpyridine, 2,3,5-collidine, potassium carbonate, cesium carbonate or tert-butanol.

5. The preparation method according to claim 1, wherein in step (1), a weight ratio of a flow rate of hydrogen per minute and the intermediate TOF-2 is 0.3-1.05 mL/g.

6. The preparation method according to claim 1, wherein the catalyst in step (1) is Pd/C, Pd(OH)$_2$/C or Pd(PPh$_3$)$_4$/C.

7. The preparation method according to claim 1, wherein in step (1), a weight ratio of the catalyst and the intermediate TOF-2 is 0.0032 to 0.0159.

8. The preparation method according to claim 1, wherein the solvent used in step (2) is toluene, ethanol, methanol, dimethylformamide, and N-methyl-2-pyrrolidone or dimethyl sulfoxide.

9. The preparation method according to claim 8, wherein the base used in step (2) is 1,8-diazabicyclo[5.4.0]undec-7-ene (DBU).

10. The preparation method according to claim 1, wherein no activated carbon is added in step (3), and a generated impurity (of the following formula TOF-IP A) is less than 0.2%

TOF IP A

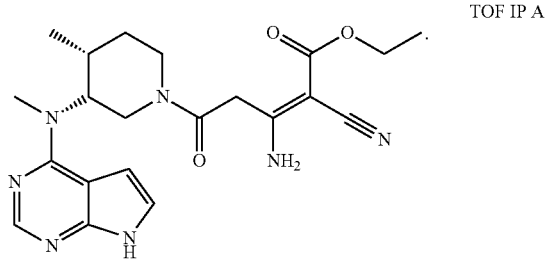

* * * * *